United States Patent

Schroeder et al.

[11] Patent Number: 5,166,747
[45] Date of Patent: Nov. 24, 1992

[54] APPARATUS AND METHOD FOR ANALYZING THE COMPOSITION OF FORMATION FLUIDS

[75] Inventors: Robert J. Schroeder, Newtown, Conn.; Jeffrey A. Tarvin, Great Shelford, United Kingdom

[73] Assignee: Schlumberger Technology Corporation, New York, N.Y.

[21] Appl. No.: 532,288

[22] Filed: Jun. 1, 1990

[51] Int. Cl.⁵ .......................... G01J 3/28; G01V 5/00
[52] U.S. Cl. ................................. 356/326; 250/343; 250/256; 356/328
[58] Field of Search .................... 250/255, 343, 256; 356/301, 326, 328; 73/155

[56] References Cited

U.S. PATENT DOCUMENTS

| | | | |
|---|---|---|---|
| 2,263,108 | 11/1941 | Stuart. | |
| 2,591,737 | 4/1952 | Souther | 250/255 |
| 2,837,960 | 6/1958 | Miller. | |
| 3,793,524 | 2/1974 | Howarth | 250/343 |
| 4,227,083 | 10/1980 | Sherinski | 250/343 |
| 4,286,327 | 8/1981 | Rosenthal et al. | 364/498 |
| 4,379,233 | 4/1983 | Rosenthal | 250/553 |
| 4,404,642 | 9/1983 | Rosenthal | 364/571 |
| 4,492,862 | 1/1985 | Grynberg et al. | 250/255 |
| 4,507,558 | 3/1985 | Bonne | 250/345 |
| 4,540,283 | 9/1985 | Bachalo | 356/336 |
| 4,633,087 | 12/1986 | Rosenthal et al. | 250/341 |
| 4,663,961 | 5/1987 | Nelson et al. | 73/24 |
| 4,769,541 | 9/1988 | Umiastowski et al. | 250/256 |

Primary Examiner—F. L. Evans
Assistant Examiner—K. P. Hantis
Attorney, Agent, or Firm—Leonard W. Pojunas

[57] ABSTRACT

A borehole apparatus for analyzing the composition of a formation fluid includes a chamber that contains the fluid, and a light source that directs light through the fluid in the chamber. The optical path of the light is modified such that an output fiber optic bundle receives indirect light through the fluid. One embodiment comprises a diffuser in the optical path, which forward scatters the light to the output fiber optic bundle. Another embodiment comprises the misalignment of an input fiber optic bundle relative to the output fiber optic bundle. Collimators can be subsituted for the fiber optic bundles.

15 Claims, 5 Drawing Sheets

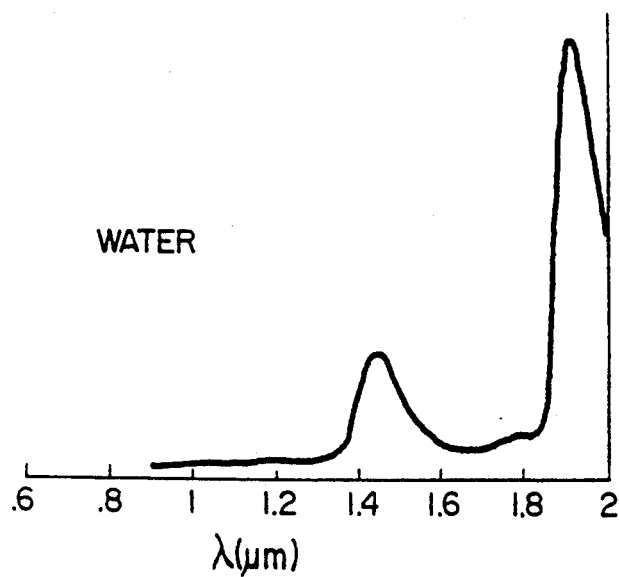
FIG. 5a  WATER
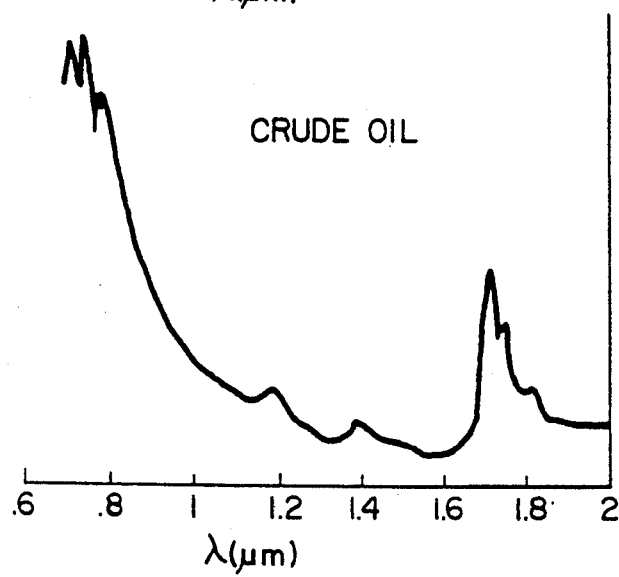
FIG. 5b  CRUDE OIL
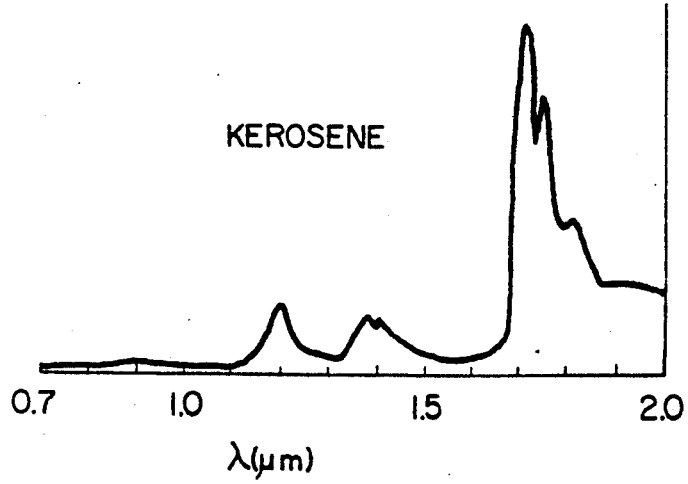
FIG. 5c  KEROSENE

APPARATUS AND METHOD FOR ANALYZING THE COMPOSITION OF FORMATION FLUIDS

BACKGROUND OF THE INVENTION

1. Technical Field

This invention relates to apparatus and methods for analyzing the composition of formation fluids, and more particularly to apparatus and methods for using near infrared spectral analysis to determine the quantities of gas, water and various types of oils in a formation fluid.

2. Background Information

As seen in FIG. 1, several different interactions may occur when light strikes a sample. Typically, if the sample is fluid, some light is reflected at the boundary of the sample while the rest of the light enters the sample. Inside the sample, light is scattered by molecular excitations (Raman scattering) and by collective modes of the medium (e.g. Rayleigh scattering). In general, only a very small fraction of the light is scattered per centimeter of the path by the Raman and Rayleigh scattering processes.

If more than one phase is present in the sample, light is elastically scattered by reflection and refraction at the boundaries between the phases. This scattering process can be quite strong as light may be scattered many times in less than one centimeter of the path. Light which is not scattered or which is scattered but emerges from the sample travelling in a direction nearly parallel to and in the same direction as the incident light is generally referred to as "transmitted". Light which emerges travelling in other directions is referred to as "scattered", while light which emerges travelling in a direction nearly opposite to the incident light is referred to as "backscattered".

Regardless of scattering, some light is absorbed by the sample. The fraction of incident light absorbed per unit of pathlength in the sample depends on the composition of the sample and on the wavelength of the light. Thus, the amount of absorption as a function of wavelength, hereinafter referred to as the "absorption spectrum", an indicator of the composition of the sample. In the wavelength range of 0.3 to 2.5 microns, which is the range of primary interest according to this invention, there are two important absorption mechanisms in borehole fluids. In the near infrared region (1 to 2.5 microns), absorption results primarily from the excitation of overtones of molecular vibrations involving hydrogen ions in the borehole fluids. In the near ultraviolet, visible, and very near infrared regions (covering wavelengths of 0.3 to 1 micron), absorption results primarily from excitation of electronic transitions in large molecules in the borehole fluids such as asphaltenes, resins, and porphyrins.

In the past, techniques have been known for the qualitative and quantitative analysis of gas, liquid, and solid samples. Methods and apparatus for accomplishing the same are disclosed in U.S. Pat. No. 4,620,284 to R. P. Schnell where a helium-neon laser is used to provide photons of a 0.633 micron wave length which are directed at a sample. The resulting Raman spectrum which comprises scattered light at different wavelengths than the incident light is then measured, and the measured spectrum is compared with previously obtained reference spectra of a plurality of substances. The provided technique is applied to monitoring fluid flowing through a pipeline in an oil refinery. In U.S. Pat. No. 4,609,821 to C. F. Summers, especially prepared rock cuttings containing at least oil from an oil-based mud are excited with UV radiation with a 0.26 micron wave length. Instead of measuring the Raman spectrum as is done in the aforementioned Schnell patent, in accord with the Summers disclosure, the frequency and intensity of the resulting excited waves (fluorescence) which are at a longer wavelength than the incident radiation are detected and measured. By comparing the fluorescent spectral profile of the detected waves with similar profiles of the oil used in the oil-based mud, a determination is made as to whether formation oil is also found in the rock cuttings.

While the Summers and Schnell disclosures may be useful in certain limited areas, it will be appreciated that they suffer from various drawbacks. For example, the use of laser equipment in Schnell severely restricts the environment in which the apparatus may be used, as lasers are not typically suited to harsh temperature and/or pressure situations (e.g. a borehole environment). Also, the use of the Raman spectrum in Schnell imposes the requirement of equipment which can detect with very high resolution the low intensity scattered signals. The use by Summers of light having a 0.26 micron wavelength severely limits the investigation of the sample to a sample of nominal thickness. In fact, the Summers patent requires that the sample be diluted with solvents before investigation. Thus, the Summers patent, while enabling a determination of whether the mud contains formation oil, does not permit an analysis of formation fluids in situ. Finally, the Summers method has no sensitivity to water.

Those skilled in the art will appreciate that the ability to conduct an analysis of formation fluids downhole is extremely desirable. A first advantage would be the ability to distinguish between formation fluids and mud filtrate, thereby permitting a fluid extraction tool to retain only fluids of interest for return to the formation surface. A second advantage is in the production phase, where a determination of the fluid type (i.e. water, oil, or gas) entering the well from the formations can be made immediately downhole.

SUMMARY OF THE INVENTION

It is therefore an object of the invention to provide a method and apparatus for analyzing the composition of a formation fluid which may include water, gas, one or more of a plurality of oils, and solid particles.

It is a further object of the invention to provide a downhole apparatus for analyzing in situ the composition of a formation fluid.

It is another object of the invention to provide an apparatus using at least the near infrared spectrum for analyzing the composition of formation fluid.

In accord to the objects of the invention, a borehole apparatus for analyzing the composition of a formation fluid generally comprises a testing region, a means for directing a sample of fluid into the region, a light source emitting at least near infrared rays, a spectral detector, a data base means, and a processing means. The testing region may, for example, comprise either a tube through which the formation fluids can flow, a chamber in which the fluid may be kept for transfer to the formation surface, or a path which interrupts light travelling through a light transmitting means. If a tube or chamber is used, the tube or chamber should include a window which is optically transparent to at least near infrared light, and preferably also to near ultraviolet and visible light. The light source may be an incandescent lamp with a known or determinable spectrum, and the emitted light is directed at least partly towards the window in the tube or chamber either via collimation or fiber optics. The spectral detector means is preferably a spectrometer which detects and measures the spectrum of the light which has been transmitted through from the fluid sample. Typically, the spectral detector means also includes directing and focussing mirrors or additional fiber optic bundles.

Knowing the spectrum of the emitted light and the spectrum of the detected light which has been affected by the fluid sample, a determination of the composition of the fluid sample may be had if a data base of the spectra of the possible components of the fluid is available. Towards that end, the spectra of water, gas, and a plurality of different oils are found and stored in a data base. Then, using a fitting technique such as a least squares analysis or a principle component analysis, a processing means (e.g. a computer or microprocessor) with access to all the information can conduct the desired fluid component analysis. Preferably, in further accordance with the principles of the invention, spectra of the oils, gas, and water at different pressures and temperatures can be maintained and used in the fitting process. Also, with regards to another aspect of the invention, a determination of a transition of the obtained fluid samples from mud filtrate to formation fluids is made by monitoring the visible light and/or near ultraviolet spectrum for changes in the same.

A better understanding of the invention, and additional advantages and objects of the invention will become apparent to those skilled in the art upon reference to the detailed description of the accompanying drawings.

BRIEF DESCRIPTION OF THE DRAWINGS

FIGS. 5a-5c show logarithmic plots of the near infrared absorption spectra of water, crude oil, and kerosene;

DESCRIPTION OF THE PREFERRED EMBODIMENTS

Figure 1:
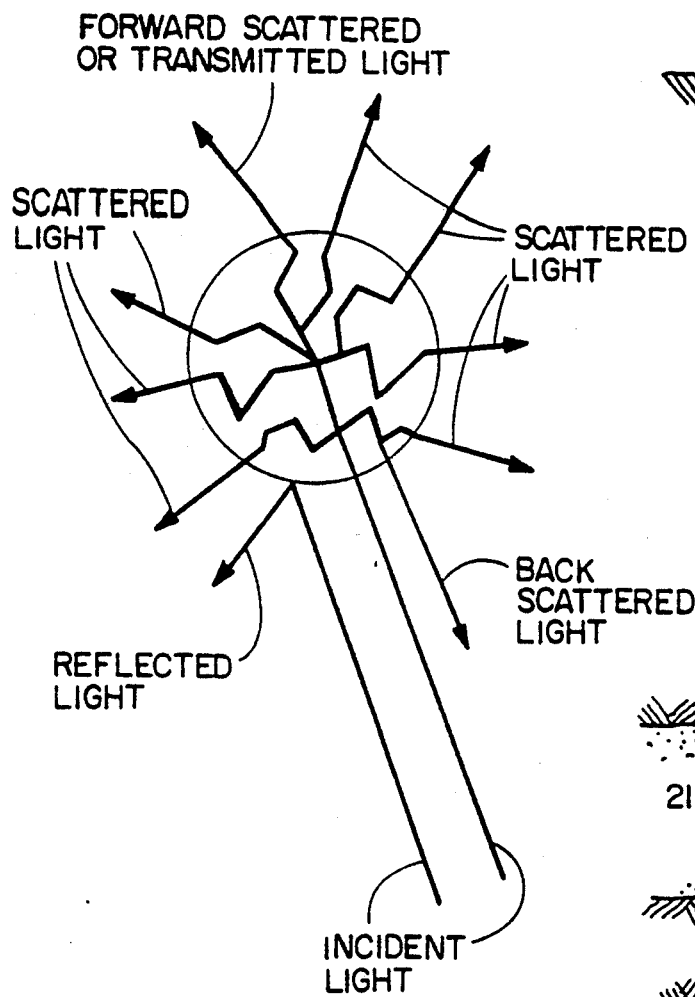
FIG. 1 is a diagram of some of the different interactions which may occur when light strikes a sample.
Figure 2:
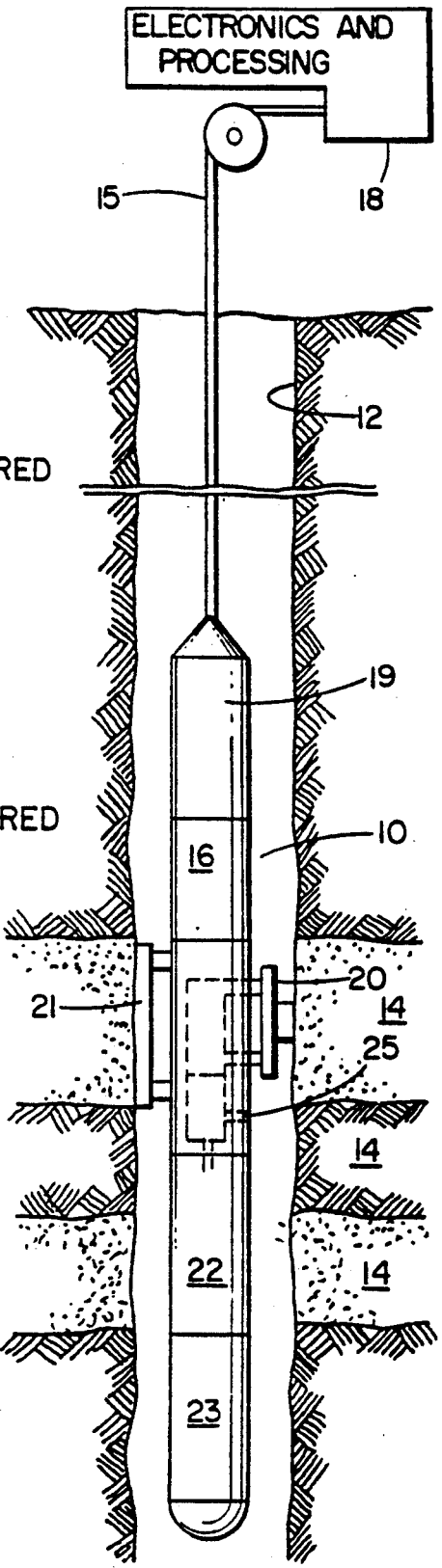
FIG. 2 is a schematic diagram of a first embodiment of a borehole apparatus for analyzing the composition of a formation fluid.

The instant invention is particularly applicable to both production logging and to borehole investigative logging. For purposes of brevity, however, the description herein will be primarily directed to borehole investigative logging. Thus, a borehole logging tool 10 for testing earth formations and analyzing the composition of fluids from the formation 14 in accord with invention is seen in FIG. 2. As illustrated, the tool 10 is suspended in the borehole 12 from the lower end of a typical multiconductor cable 15 that is spooled in the usual fashion on a suitable winch (not shown) on the formation surface. On the surface, the cable 15 is electrically connected to an electrical control system 18. The tool 10 includes an elongated body 19 which encloses the downhole portion of the tool control system 16. The elongated body 19 also carries a selectively extendible fluid admitting assembly 20 and a selectively extendible tool anchoring member 21 which is respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18. Additional details of methods and apparatus for obtaining formation fluid samples may be had by reference to U.S. Pat. No. 3,859,851 to Urbanosky and U.S. Pat. No. 3,813,936 to Urbanosky et al. and U.S. Pat. No. 3,811,321 to Urbanosky assigned to the assignee herein. It should be appreciated, however, that it is not intended that the invention be limited to any particular method or apparatus for obtaining the formation fluids.

Figure 3:
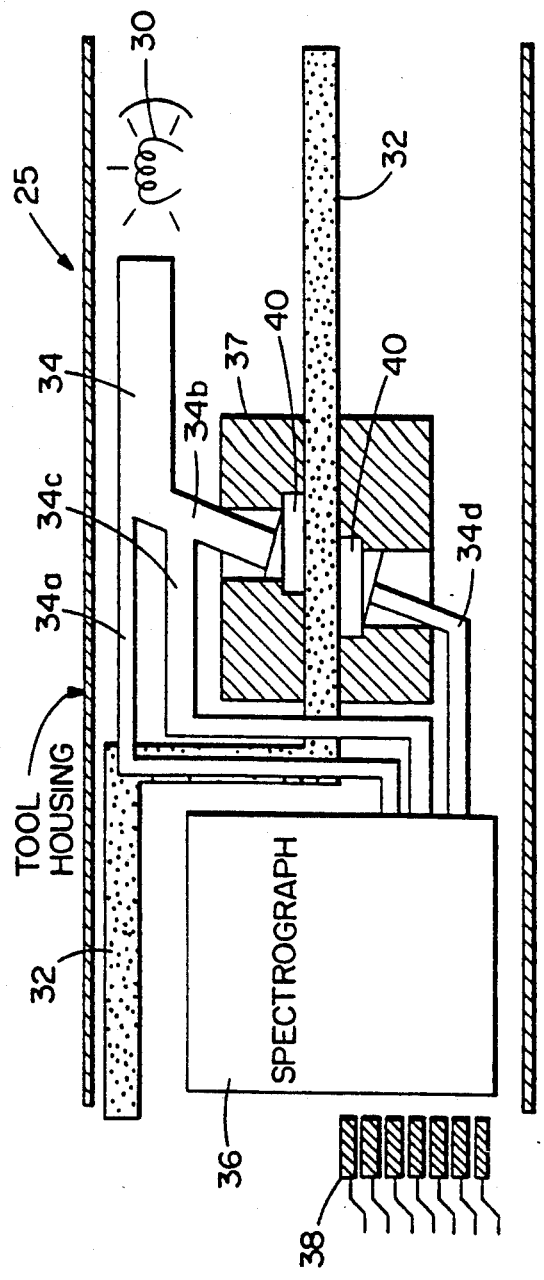
FIG. 3 is a schematic diagram of the preferred near infrared fluid analysis module of FIG. 2.
Figure 4:
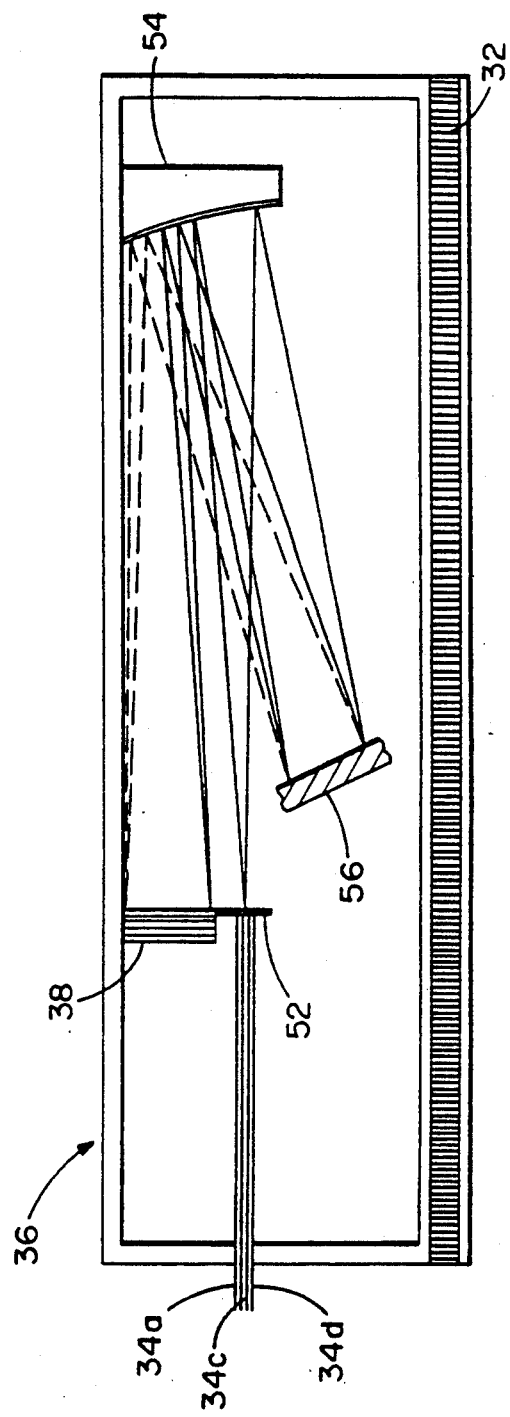
FIG. 4 is a schematic diagram of the preferred spectrometer of the invention.

Turning to FIG. 3, the preferred fluid analysis module 25 is seen in detail and preferably includes a light source 30, a fluid sample tube 32, optical fibers 34, and a spectrograph 36 and associated detector array 38. The light source 30 is preferably an incandescent tungsten-halogen lamp which is kept at near atmospheric pressure. The light source 30 is relatively bright throughout the near infrared wavelength region of 1 to 2.5 microns and down to approximately 0.5 microns, and has acceptable emissions from 0.35 to 0.5 microns. Light rays from the light source 30 are preferably transported from the source to the fluid sample by at least part of a fiber optic bundle 34. The fiber optic bundle 34 is preferably split into various sections. A first section 34a goes directly from the light source 30 to the spectrograph 36 and is used to sample the light source. A second section 34b is directed into an optical cell 37 through which the sample tube 32 runs and is used for illuminating the fluid sample. A third section 34c originates at the cell 37 and goes directly to the spectrograph 36 and is used to collect light substantially backscattered by the sample. Spectral information obtained by section 34c is helpful in determining the composition of the sample fluid, and in conjuction with a fourth bundle 34d in determining whether gas is present as will be discussed hereinafter. A fourth bundle 34d collects light transmitted or scattered through the sample and also provides information regarding the nature of the fluid flowing through the sample tube or chamber 32. A three position solenoid (not shown) is used to place on of bundles 34a, 34c and 34d at the input slit (seen in FIG. 4) of the spectrograph, and a light chopper (not shown) modulates the signal at 500 Hz to avoid low frequency noise in the detectors.

As aforementioned, optical bundle 34b directs the light towards the fluid sample. The fluid sample is obtained from the formation by the fluid admitting assembly and then is sent to the fluid analysis section 25 in tube 32. In a preferred embodiment, the sample tube 32 is a three by four millimeter rectangular channel. The tube preferably includes a section 40 with windows made of sapphire. This section 40 is located in the optical cell 37 where the light rays are arranged to illuminate the sample. Sapphire is chosen as it is substantially transparent to the spectrum of the preferred light source. Also, sapphire is preferable because it is much harder than silica and resists abrasion. As indicated in FIG. 3, the sapphire window areas 40 of tube 32 may be arranged to be thick so as to withstand high internal pressure, and the window areas are offset slightly so that they are kept centered on the path of the transmitted light. The fiber optic bundle 34b is not perpendicular to the flow stream so as to ensure that specular reflection does not enter fiber optic bundle 34c, because specular reflection (reflection due to the interface of the sapphire wall and the liquid sample) does not provide useful information. As a result of the arrangement, optic bundle 34c will receive and conduct substantially backscattered light.

As previously indicated, the fiber optic bundles 34a, 34c and 34d terminate at the spectrograph 36. As seen in detail in FIG. 4, the spectrograph includes an entrance slit 52, an off-axis paraboloidal mirror 54, a diffraction grating means 56, and the detector array 38. Light exiting the chosen fiber optic bundle and entering the spectrograph 36 via slit 52 reflects off the off-axis paraboloidal mirror 54 towards a blazed diffraction grating 56. The blazed diffraction grating disperses and diffracts the light into a small range of angles, with rays of different wavelengths being diffracted differently. The diffracted and dispersed light is directed back toward a section of the off-axis paraboloidal mirror which causes the rays of different wavelengths to be reflected and focussed on different elements of the detector array 38. The detector array elements may therefore determine the intensity of the light entering the spectrograph as a function of wavelength. The information may then be multiplexed to a digitizer and prepared for transmission uphole to electronics and processing means 18.

Preferably, the off-axis paraboloidal mirror 54, the diffraction grating 56, and any mounting fixtures (not shown) used to mount them are all made of aluminum so that the thermal expansion of the components will be identical. This arrangement would ensure that the angular relations among the components would not change with temperature. As a result, the position of a given wavelength at the detector plane would be independent of temperature.

With the provided fluid analysis section 25, the spectra of the light source, of the backscattered light which has scattered off the fluid sample, and of the forward scattered and transmitted light may be determined. When the transmitted light spectrum and the backscattered light spectrum are divided by the source spectrum, two absorption spectra (one for transmitted, one for backscattered) are obtained. The absorption spectrum of the transmitted light is preferably used in the hereinafter-described analysis if its count rate is sufficient. Otherwise, the backscattered absorption spectrum (or both) may be used.

Because different materials have different absorption characteristics, it becomes possible to make a determination as to what materials comprise the fluid sample, provided, of course, that the spectra of the materials which might be in the fluid sample are known. Towards that end, the spectra of water, gas, and a plurality of different oils are found in accord with techniques well known in the art. Examples of such spectra are seen FIG. 5a, water has absorption peaks at about 1.5 and 1.9 microns. As seen in FIG. 5b, crude oil has an absorption peak at 1.7 microns. The particular crude oil shown in FIG. 5b has increasing absorption for wavelengths less than 1.6 microns. Many crude oils have a similar feature, but the onset is often at shorter wavelengths. Refined oils such as kerosene shown in FIG. 5c, are generally transparent between 0.7 and 1.1 microns. However, like crude oil, they typically have an absorption peak at 1.7 microns and other features which appear in crude oil at 1.2 and 1.4 microns.

Using the absorption spectra of water, gas, crude and refined oils, and drilling fluids (muds), a least squares analysis such as is described generally in Bevington, Philip R., *Data Reduction and Error Analysis for the Physical Sciences*, McGraw-Hill Book Co., New York (1969), may be used to determine the components of the fluid sample. Or, if desired, a principle component analysis such as is described generally in Williams, P.C., et al., *J. Agricultural Food Chemistry*, Vol. 33, pg. 239 (1985), could be used in a similar manner to determine the components of the fluid sample. The analysis is preferably conducted in a processing means such as a computer which is located uphole in the electronics and processing circuitry 18.

With regard to the fitting technique used to determine the fluid components, not only may a single spectrum for water, gas, oils, etc. be used in the data base, but, if desired, both transmission and backscattered absorption spectra may be utilized for each. Moreover, it will be appreciated that the spectra of the various components may vary with temperature and pressure. Thus, not only should the spectra of water, gas, and a plurality of oils be used as reference spectra, but a plurality of different spectra for each different material at different pressures and temperatures (and if desired for transmission and backscatter) should be available for an accurate determination of the fluid components to be made.

Those skilled in the art will appreciate that natural gas has a similar spectral shape to certain oils. On the other hand, because gas has a low density, only a small fraction of the light having a wavelength range of 0.3 to 2.5 will be absorbed by the sample. Thus, in accord with another aspect of the invention, the spectrum obtained by fiber optic bundle 34c may be compared to the spectrum obtained by fiber optic bundle 34d, to give a first indication of the percent gas contained in the sample. Having such an indication permits a more complete fitting of the different spectra even if the gas spectrum is very similar to one or more of the oil spectra.

Also, in accord with another aspect of the invention, the visible light and/or near-ultraviolet spectrum, preferably from 0.3 to 1 micron in wavelength, may be used to obtain indications of large molecules in a fluid such as porphyrins, asphaltenes, large aromatics, and resins. While these large molecules are present in low concentrations, they are easy to observe due to the absorption by their electronic transitions. Because the concentration and kind of large molecules in mud filtrates and formation fluids usually differ, a correlation of the large molecule 0.3 to 1 micron spectra provides an indication as to whether the fluid sample flowing through the optical cell 37 is changing over time. Since the first fluid to enter the cell 37 typically is the drilling fluid, the sample may be expelled rather than stored in chambers 22 or 23. Likewise, after the large molecule spectra indicate a change in fluid type (even through the NIR spectra for the oil and/or water in the fluid remain substantially the same as might be the case with an oil based mud filtrate and formation oil), the sample may be identified as a formation fluid sample, and the sample may be forwarded from the fluid analysis module 25 to the storage chambers for delivery uphole.

In connection with yet another aspect of the invention, the obtained spectra as well as the determination of the presence of gas may be used to control the pressure of the flow line so as to obtain a more representative sample of the formation fluid. In the situation where the formation fluid is comprised of both heavy and light hydrocarbons, bubbles of the lighter hydrocarbon can evolve out of the fluid, or the heavier hydrocarbons can condense out of the fluid. When the pressure of the fluid is below either the bubble point pressure or the dew point pressure (depending on the case) the fluid emerges from the formation in both the liquid and vapor phase. Since the less viscous vapor phase flows more freely than the liquid phase, the obtained sample includes more light hydrocarbons than is representative of the formation fluid. By changing the pressure in the flow line which is accomplished by standard techniques, the bubble point or dew point may be found as both of these effects will result in a decrease of transmitted light and an increase of backscattered light. The monitoring of transmission and reflection is best accomplished at a wavelength at which absorption is weak and at which the sample is relatively transparent. Once the bubble point or dew point pressure is found, the pressure of the flow line (sampling pressure) is increased above the relevant point by e.g., controlling the rate at which fluid flows through the sampling apparatus and/or locating the sampling apparatus at an appropriate depth in the well.

Figure 6:
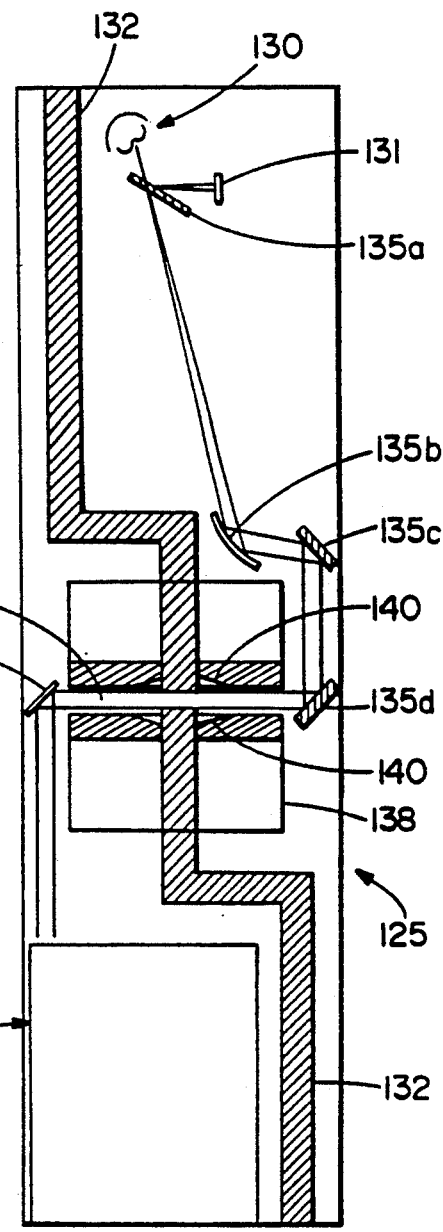
FIG. 6 is a schematic diagram of an alternative near infrared fluid analysis module of FIG. 2.

Turning to FIG. 6, an alternative embodiment 125 of the fluid analysis module 25 of the borehole apparatus 10 is seen. Basically, the fluid module components are the same as the preferred embodiment, except that instead of using optical fiber bundles, directing and focussing mirrors are used. In accord with the embodiment of FIG. 6, the source 130 is identical to that used in the preferred embodiment. The source is partially reflected by beam splitting mirror 135a to a reference detector 131 where a determination of the source spectrum downhole may be had. The non-reflected light is forwarded to collimating mirror 135b. The collimated light is then forwarded via directing mirrors 135c and 135d towards the optical cell 138 which is comprised of a high pressure stainless steel chamber with a fluid sample tube 132 passing therethrough, and with an optical path 139 perpendicular to and interrupted by the tube 132 also passing therethrough. In optical cell 138, the fluid sample tube 132 has sapphire windows 140. Light passing from mirror 135d into optical path 139, and either transmitted or scattered through the fluid sample exits the optical cell 138 and is directed by mirror 135e to the spectrometer (spectrograph) 136 which is preferably similar to the aforedescribed spectrograph 36 of FIG. 4. If desired, the spectrometer 136 may be used in lieu of the reference detector 131, provided suitable optical means (not shown) are used to transport light directly from the source to the spectrometer and other means (multiplexing) are used to select either the light from the source or the light from the optical cell. Additionally, backscattered light may be analyzed by the spectrometer if mirror 135c is replaced by a suitable beam splitter and additional suitable optical means (not shown) are used to transport the backscattered light to the spectrometer. With such additional optical means, it will be appreciated that the embodiment of FIG. 6 becomes the functional equivalent of the embodiment of FIG. 4, with fiber optics being replaced by reflective optics.

Figure 7:
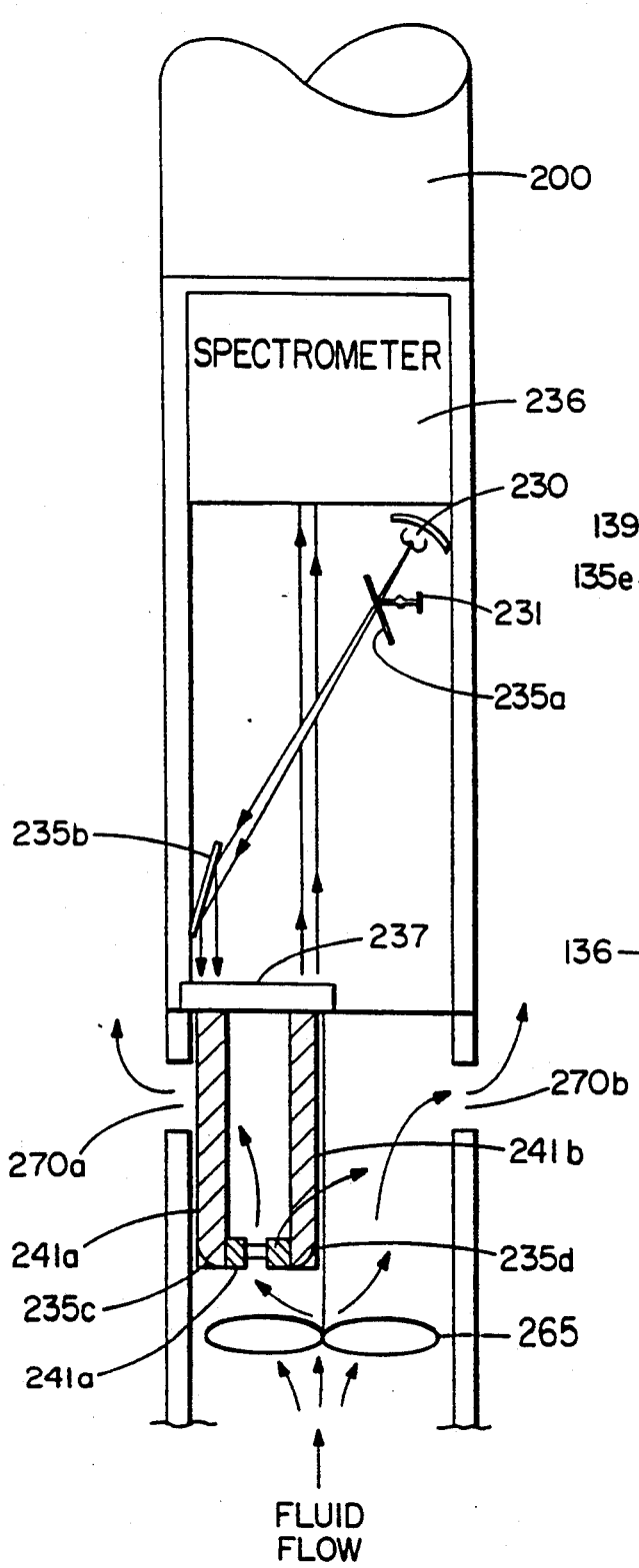
FIG. 7 is a schematic diagram of the fluid analysis module of the invention which is used in conjunction with a production logging tool.

Turning to FIG. 7, a fluid analysis module 225 of a production logging tool is seen. The theoretical basis for the fluid analysis module 225 is identical to the fluid analysis modules of FIGS. 3 and 6. However, instead of providing a fluid admitting assembly for obtaining fluid samples from the formation and chambers for storage of the obtained samples, fluid is already flowing through the tool 200. As in the previously discussed modules, the fluid analysis module 225 uses a quartz halogen lamp as a light source 230. As in the embodiment of FIG. 6, a beam splitter mirror 235a is used to permit a reference detector 231 to sense and determine the spectrum of the source, and to send on the beam towards the fluid to be sampled. The beam is directed by collimating mirror 235b through a sapphire window 237 and then through a sapphire rods 241a having reflective surface or mirror 235c contained therein. The beam is then directed through a fluid sample which is obtained by mixing fluid by spinner 265, and having some of the fluid passing through an opening of approximately five millimeters between the sapphire rods 241a and 241b (the opening comprising a "testing region". The fluid then exits the fluid analysis module 225 through ports 270a and 270b in the wall of tool 200. The light which is transmitted or scattered through the fluid is then transmitted through sapphire rod 241b which includes a reflective surface or mirror 235d, out through sapphire window 237 and directly to spectrometer 236. Again, spectrometer 236 is preferably a spectrograph as shown in FIG. 3, and the spectrometer may be used as the reference detector. Also, as was described with reference to FIG. 6, the backscattered light may also be directed to the spectrometer by a suitable arrangement of reflective optics.

In operation, the borehole logging tool 10 shown in FIGS. 2 and 3 is placed downhole via extended cable 15. At a desired location, electronic section 18 provides signals to electronic section 16 which causes anchoring member 21 and admitting assembly 20 to extend into contact with the borehole walls. Upon a second signal from electronic section 16, and in accord with known tools in the art, formation fluid is obtained by the admitting assembly 20 and forwarded into the sample tube 32 of the fluid analysis module 25. Concurrently, light emitted by an optical source 30 is carried via optical fibers 34 to optical cell 37 where it is transmitted through, scattered by, and absorbed by the fluid sample. Forward scattered light, and light transmitted through the sample are forwarded to the spectrograph 36 where the transmitted, forward scattered spectrum is separated into its component wavelengths. Also, preferably, backscattered light and a spectral sample of the optical source are forwarded to the spectrograph 36 via a fiber optical bundle for division into its wavelength components. Each spectrum is sampled in order (the source spectrum not necessarily being sampled as often). Then, using detector array 38 and electronic section 16, the different spectral information is forwarded uphole to electronic and processing section 18 for analysis. Also, if desired, fluid temperature and pressure information may also be forwarded uphole. Preferably, using a least squares fit, the processor in processing section 18 fits the obtained spectra (with wavelengths from 0.3 to 2.5 microns) to a plurality of temperature-and pressure-specific absorption spectra for oils, water, and gas which are stored in a data base accessible to the processor. As a result of the fitting process, a determination is made of the components which comprise the fluid sample. A log of such a determination over borehole depth can then be made.

As indicated above, if both backscatter and forward scatter and transmission information is obtained, a first indication of the presence of gas may be had. This first indication may then be used to help in the fitting process. Also, if desired, using the spectrum from approximately 0.3 microns to 1 micron, a determination of whether a change has occurred in the types and/or quantities of large molecules may be had by using a correlation technique. The determination of whether a fluid change has occurred may then be used by the processor 18 via electronic section 16, to cause the fluid sample to be expelled into the borehole or to be forwarded into holding chambers 22 or 23 for further uphole analysis.

Figure 8:
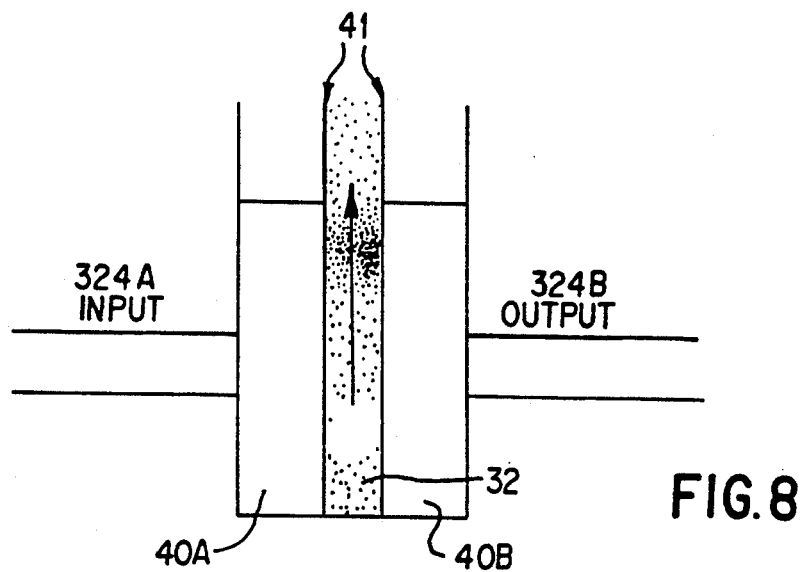
FIG. 8 is a schematic diagram of one embodiment of the optic cell in FIG. 3, illustrating the use of diffusers.

FIG. 8 is a schematic diagram of the optic cell of FIG. 3. A fiber optic bundle 324A carries light from a light source, such as the source 30 of FIG. 3, to a first window section 40A. The window section 40A comprises a portion of a sample tube 32 through which a fluid sample flows. The sample tube 32 also comprises a chamber for containing the fluid sample. The fluid sample is illustrated by varying shades of grey in the sample tube 32.

Light carried by the fiber optic bundle 324A passes through the fluid sample in the sample tube 32 and is scattered by the fluid sample. The amount of light that is scattered by the fluid sample depends on the composition of the fluid sample. In a multiphase flow stream, such as formation fluid, the composition of the flow stream varies greatly because the composition of the flow stream is not at all uniform. For example, the flow stream will include, among other things, bubbles of gas, particles of sand, and globules of oil. Gas, illustrated by the light area 41A, flowing in the sample tube 32 scatters the light to a small degree as the gas flows by the window section 40A. Because the light is scattered to a small degree, a relatively high intensity light signal passes through the fluid sample and reaches a second window section 40B. Conversely, sand, illustrated by the dark area 41B, flowing in the sample tube 32 scatters the light from the fiber optic bundle 324A to a greater degree as the sand flows by the window sections 40A. Because the light is scattered to a greater degree, a lower intensity light signal reaches the window section 40B. A second fiber optic bundle 324B carries the resulting light signal from the window section 40B to the spectograph 36 of FIG. 3 for analysis. Because the degree of scattering can change abruptly as different phases of fluid pass by the window sections 40A and 40B, great swings occur in the intensity of the light signal that passes through the fluid sample. The spectograph, which receives such signals, must be designed to accommodate these swings in order to process the information that the light signal represents.

Accordingly, the inventors have developed a technique and device for minimizing the effects of such large signal swings. The technique and device concerns the measurement of indirect transmitted or forward scattered light instead of direct transmitted light. Measuring indirect transmitted light results in a light signal having a more consistent amplitude that is less affected by variations in flow patterns and phase changes within the sample tube 32, for example. In creating a light signal having a more constant amplitude, a significant reduction in signal swing occurs.

Figure 8A:
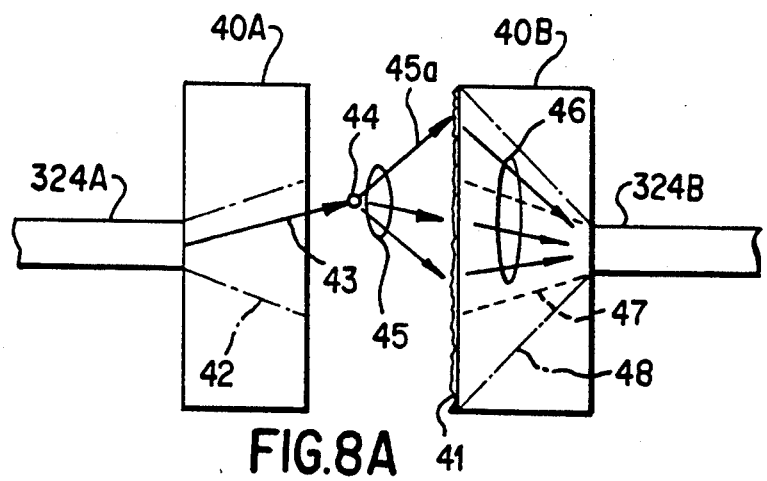
FIG. 8a is a diagram illustrating the effect a diffuser in FIG. 8 has on a light ray.
Figure 9:
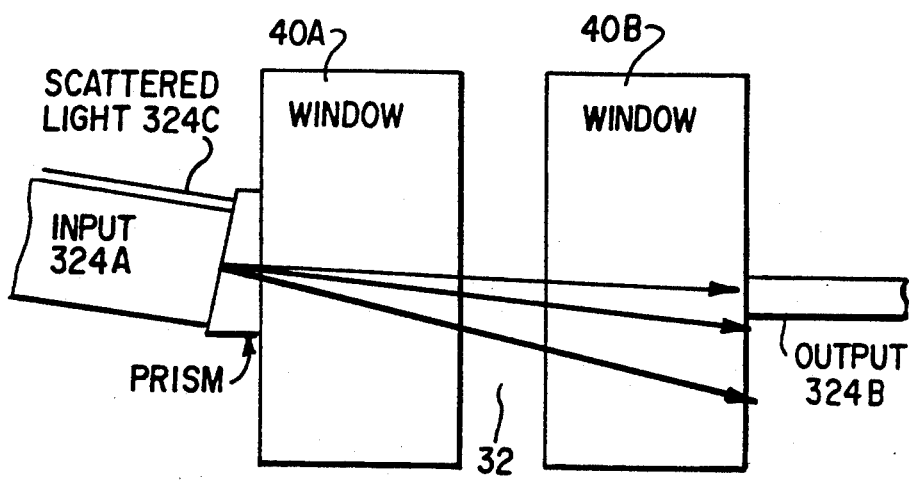
FIG. 9 is a schematic diagram of another embodiment of the optic cell in FIG. 3, illustrating the use of misalignment.

FIGS. 8A and 9 show two preferred embodiments of the invention that compensate for the effects of signal swing by modifying the optical path of light from the input fiber optic bundle 324A and the window section 40A through the fluid sample to the window section 40B and the output fiber optic bundle 324B. These embodiments alter the optical path of light through the fluid sample to allow the detection and measurement of substantially indirect transmitted light.

FIG. 8A shows the second window section 40B of FIG. 8 having a diffuser 41. The diffuser 41 is a distinct element that is attached to or, preferably, is formed directly on the surface of the window section 40B. The diffuser 41 is formed by scoring or etching the surface of the window section 40B. The diffuser on the window section 40B increases the collection angle of light that passes through the fluid.

Light from the fiber optic bundle 324A enters the window section 40A and exits as a broadening beam 42 of light that passes into fluid contained in the sample tube 32. One light ray 43 of the beam 42 hits a sand particle 44 or oil droplet in the fluid, for example. Many sand particles are present in the fluid, but only one is shown in FIG. 8A for simplicity. The sand particle 44 in the fluid scatters the light in many directions. Forward scattered light 45 is transmitted toward the far side of the sample tube 32. The diffuser 41 collects the light that scatters from the sand particle 44 and redirects a substantial amount of the collected light 46 toward the output fiber optic bundle 324B. The diffuser 41 reduces the intensity of light from the fiber optic bundle 324A that is directly transmitted through the fluid sample in the sample tube 32 to the fiber optic bundle 324B, for instance. However, the diffuser 41 changes the solid angle of emission of the scattered ray from the sand particle thereby providing an effective wider angle of light acceptance 47 for the output fiber optic bundle 324B. Without the diffuser 41, a narrow angle of light acceptance 47, which is determined by the numerical aperture of the output fiber optic bundle 324B, would collect less of the light that was scattered by the sand particle in the fluid.

For example, in the case of a window section 40B having no diffuser, a ray of light 45a would be scattered by the sand particle 44 outside the angle of acceptance 47. Thus, the scattered light ray 45a would never reach the output fiber optic bundle 324B. However, according to this invention, the light ray 45a is scattered by the sand particle 44 to the diffuser 41, which again scatters or redirects the light ray 45a within the angle of acceptance 46 of the output fiber optic bundle 324B.

The intensity of light that passes through the diffuser 41 and reaches the fiber optic bundle 324B is substantially less than the intensity of light that would be directly transmitted from a light input through a chamber and to a light output, for example. This light of less intensity produces a weaker signal to the spectograph.

However, this weaker signal is accepted as a tradeoff for signal stability.

Instead of a diffuser, a collecting lens can decollimate the forward scattered light onto the output fiber optic bundle 324B. A diffuser can also be formed on the surface of the first window section 40A alone, or in addition to the window section 40B to broaden the angle of light transmitted from the window section 40A and broaden the angle of light acceptance of the output optic fiber bundle 324B. The diffuser 41 can also be formed on the end of either fiber optic bundle 324A or 324B or on the prisms of FIG. 3.

FIG. 9 shows an embodiment in which the output fiber optic bundle 324B is misaligned relative to the input fiber optic bundle 324A to modify the optic path of light transmitted through the sample fluid in the sample tube 32. These bundles are misaligned in that the longitudinal axis of the bundles are not collinear or parallel. In a preferred embodiment, the fiber optic bundle 324B connects to the window section 40B through a prism and parallels the fiber optic bundle 324A, as FIG. 3 illustrates. FIG. 9 shows the fiber optic bundle 324B without a prism for simplicity.

The misalignment of input and output bundles reduces the amount of light from the fiber optic bundle 324A that is directly transmitted through the fluid sample in the sample tube 32 to the fiber optic bundle 324B, because the directly transmitted light, illustrated by a thick arrow, misses the output fiber optic bundle 324B. Only indirect light, illustrated by a thin arrow, reaches the output fiber optic bundle 324B. Compared to an optic cell system having parallel and offset input and output fiber optic bundles, the system of FIG. 9 reduces the amount of indirect light entering the fiber optic bundle 324B when the fluid between the window sections 40A and 40B comprises a gas bubble, but increases the amount of indirect light entering that bundle when the fluid comprises a particle of sand, for instance. This allows the spectograph to receive a relatively constant signal which is, therefore, not easily affected by flow variation within the sample tube 32. Thus, measuring the forward scattered, indirect transmitted light results in a large reduction in signal swing, and a reduction in overall signal level.

A scattered light fiber optic bundle 324C transmits any backscattered light, such as that which reflects off of sand particles in the sample tube 32, to the spectograph 36 of FIG. 3 for reflection spectroscopy. The spectograph uses the signals of the bundle 324C, along with the signals of the output fiber optic bundle 324B in analyzing the formation fluid in the sample tube 32.

We claim:

1. A borehole apparatus for analyzing the composition of a fluid obtained from a formation, the fluid comprising at least one of water, oil, and gas, the apparatus comprising:

a light source for emitting light comprising a spectrum of frequencies and having an optical path;

a chamber means for containing the fluid and including a first portion that is substantially transparent to the light;

a light input means for directing light from the source through the first portion into the fluid;

a light output means for receiving light from the fluid in the chamber means;

means, connected between the light input means and the light output means, for modifying the optical path of the light between the light input means and the light output means, such that the light received by the light output means substantially comprises light that passes indirectly through the fluid in the chamber means;

detector means for detecting the spectrum of the light from the light output means;

storing means for storing absorption spectral information of at least two of water, oil, and gas; and processing means for receiving the spectrum of light from the source, the spectrum detected by the detector means, and the absorption spectral information of the storing means, and for determining the composition of the fluid therefrom.

2. The apparatus of claim 1, the means for modifying the optical path comprising a diffuser that diffuses the light transmitted through the fluid.

3. The apparatus of claim 2, the chamber means having a second portion through which the light from the fluid passes to the light output means.

4. A method for analyzing in a borehole the composition of a fluid obtained from a formation, the fluid comprising at least one of water, oil, and gas, comprising the steps of:

containing the fluid in a chamber having a first portion that is substantially transparent to light;

directing light comprising a spectrum of frequencies along an optical path with a light input, the optical path including the first portion and the fluid;

modifying the optical path of the light between the light input and a light output with a means connected between the light input and the light output;

receiving substantially indirect light from the fluid in the chamber with the light output;

detecting the spectrum of the light from the light output with a detector;

storing absorption spectral information of at least two of water, oil, and gas; and receiving and processing the spectrum of light from the source, the spectrum detected by the detector, and the absorption spectral information to determine the composition of the fluid.

5. The method of claim 4, the step of modifying the optical path comprising diffusing the light that is transmitted.

6. The method of claim 4, the step of modifying the optical path comprising misaligning the light input relative to the light output.

7. The method of claim 6, the step of modifying the optical path comprising misaligning fiber optic bundles that comprises the light input and the light output.

8. A borehole apparatus for analyzing the composition of a fluid obtained from a formation, the fluid comprising at least one of water, oil, and gas, the apparatus comprising:

a light source for emitting light comprising a spectrum of frequencies and having an optical path;

a chamber means for containing the fluid and including a first portion that is substantially transparent to the light and a second portion that is substantially transparent to light from the source;

a light input means for directing light from the source through the first portion into the fluid;

a light output means for receiving light from the fluid in the chamber means;

a diffuser, connected between the light input means and the light output means, for modifying the optical path of the light between the light input means and the light output means such that the light received by the light output means substantially comprises light that has been diffused through the fluid in the chamber means;

detector means for detecting the spectrum of the light from the light output means;

storing means for storing absorption spectral information of at least two of water, oil, and gas; and processing means for receiving the spectrum of light from the source, the spectrum detected by the detector means, and the absorption spectral information of the storing means, and for determining the composition of the fluid therefrom.

9. The apparatus of claim 8, wherein the diffuser comprises an irregular surface.

10. The apparatus of claim 9, wherein the irregular surface comprises a scored surface.

11. The apparatus of claim 9, wherein the irregular surface comprises an etched surface.

12. A borehole apparatus for analyzing the composition of a fluid obtained from a formation, the fluid comprising at least one of water, oil, and gas, the apparatus comprising:

a light source for emitting light comprising a spectrum of frequencies and having an optical path;

a chamber means for containing the fluid and including a first portion that is substantially transparent to the light;

a light input means for directing light from the source through the first portion into the fluid;

a light output means for receiving light from the fluid in the chamber means;

means for connecting the light input means and the light output means, in an optical path of light between the light input means and the light output means, such that the light input means is misaligned relative to the light output means and such that the light received by the light output means substantially comprises light that passes indirectly through the fluid in the chamber means;

detector means for detecting the spectrum of the light from the light output means;

storing means for storing absorption spectral information of at least two of water, oil, and gas; and processing means for receiving the spectrum of light from the source, the spectrum detected by the detector means, and the absorption spectral information of the storing means, and for determining the composition of the fluid therefrom.

13. The apparatus of claim 12, the light input means and the light output means comprising misaligned fiber optic means.

14. A method for analyzing in a borehole the composition of a fluid obtained from a formation, the fluid comprising at least one of water, oil, and gas, comprising the steps of:

containing the fluid in a chamber having a first portion that is substantially transparent to light;

directing light comprising a spectrum of frequencies along an optical path with a light input, the optical path including the window and the fluid;

modifying the optical path of the light between the light input and a light output with a means connected between the light input and the light output by diffusing the light that is transmitted with a second portion of the chamber that is substantially transparent to light and has an irregular surface;

receiving substantially indirect light from the fluid in the chamber with the light output;

detecting the spectrum of the light from the light output with a detector;

storing absorption spectral information of at least two of water, oil, and gas; and receiving and processing the spectrum of light from the source, the spectrum detected by the detector, and the absorption spectral information and determining the composition of the fluid thereby.

15. The method of claim 14, comprising passing the light through the second portion of the chamber to the light output means.

* * * * *